United States Patent [19]

Ouchi et al.

[11] Patent Number: 5,524,619
[45] Date of Patent: Jun. 11, 1996

[54] MULTIELECTRODE PROBE

[75] Inventors: Teruhiko Ouchi; Kunimasa Katayama; Hiroshi Shimane, all of Kanagawa-ken, Japan

[73] Assignee: Terumo Kabushiki Kaisha, Tokyo, Japan

[21] Appl. No.: 219,380

[22] Filed: Mar. 29, 1994

[30] Foreign Application Priority Data

Apr. 1, 1993 [JP] Japan ..................... 5-075543

[51] Int. Cl.$^6$ .......................................... A61B 5/042
[52] U.S. Cl. .......................................... 128/642
[58] Field of Search ................ 128/642; 607/119, 607/122–128

[56] References Cited

U.S. PATENT DOCUMENTS

| | | | |
|---|---|---|---|
| 3,568,660 | 3/1971 | Crites et al. | 607/122 |
| 4,073,287 | 2/1978 | Bradley et al. | 128/642 |
| 4,437,474 | 3/1984 | Peers-Traverton | 607/119 |
| 4,514,589 | 4/1985 | Aldinger et al. | 174/119 R |
| 4,559,951 | 12/1985 | Dahl et al. | 607/122 |
| 4,630,611 | 12/1986 | King | 128/642 |
| 4,633,889 | 1/1987 | Talalla et al. | 128/642 |
| 4,660,571 | 4/1987 | Hess et al. | 128/784 |
| 4,890,623 | 1/1990 | Cook et al. | 128/642 |
| 5,071,428 | 12/1991 | Chin et al. | 606/184 |
| 5,327,889 | 7/1994 | Imran | 607/122 |
| 5,411,025 | 5/1995 | Webster, Jr. | 607/122 |

FOREIGN PATENT DOCUMENTS

| | | | |
|---|---|---|---|
| 0073881 | 3/1983 | European Pat. Off. | |
| 0491979 | 12/1990 | European Pat. Off. | 607/122 |
| 2494118 | 5/1982 | France | 607/122 |
| 3215021 | 10/1983 | Germany | 607/122 |
| 64-20841 | 1/1989 | Japan . | |
| 3-236833 | 10/1991 | Japan . | |
| 5-502816 | 5/1993 | Japan . | |
| WO91/19452 | 12/1991 | WIPO . | |

OTHER PUBLICATIONS

Johnston et al, "Body Tissue Transducer" IBM Technical Disclosure Bulletin, Jan. 1964.

*Primary Examiner*—Lee S. Cohen
*Attorney, Agent, or Firm*—Burns, Doane, Swecker & Mathis

[57] ABSTRACT

A multielectrode probe of this invention is inserted into a patient when in use. This probe includes a base on which a plurality of signal lines are bonded. Each of the plurality of signal lines has at least one electrode, and these electrodes are arranged on the base with predetermined spacings between them. The electrodes are formed by stripping the isolating coatings of the plurality of signal lines.

17 Claims, 9 Drawing Sheets

MULTIELECTRODE PROBE

BACKGROUND OF THE INVENTION

1. Field of the Invention

The present invention relates to a multielectrode probe for use in an electrophysiology test performed prior to therapies for tachycardiac arrhythmia such as Wolff-Parkinson-White syndrome or paroxysmal supraventricular tachycardia, and a method of manufacturing the same.

2. Description of the Related Art

Conventionally, an electrophysiology test performed prior to therapies for tachycardiac arrhythmia is performed by using a plurality of cardiac catheters. The arrangement of each cardiac catheter is that one or two to six electrodes are formed around the tip of a hollow catheter, and lead wires are extended through this hollow catheter and connected to a measurement device. Measurements for a left heart portion are performed by inserting the catheter into a coronary sinus. However, since it is difficult to insert the catheter into a right coronary artery, measurements for a right heart portion must be performed by moving the position one point after another from inside a ventricle, resulting in a very cumbersome examination. Consequently, one examination requires a few hours.

This conventional examination method further has the following problems. First, since the examination is done by using the catheters each having few electrodes, finding a portion to be diagnosed, such as an accessory pathway, is time-consuming. In addition, since the number of the electrodes is small, the distance between the individual electrodes must be increased to measure a wide region. This makes it difficult to accurately find the accessory pathway. Furthermore, the use of a plurality of catheters imposes a large load on a patient.

To solve the above problem that a portion to be diagnosed is difficult to find, it may be possible to increase the number of electrodes. If, however, the number of electrodes of the conventional electrode catheter is increased, the number of signal lines for transmitting signals must also be increased, resulting in a large outer diameter of the catheter. This consequently makes it difficult to insert the catheter into a right coronary artery in examining a right heart portion. In addition, since an electrode is formed at the end of a signal line, an operation for connecting the signal line and the electrode is required. This makes the manufacture of a multielectrode catheter more difficult.

SUMMARY OF THE INVENTION

The present invention has been made in consideration of the above conventional situations and has its object to provide a multielectrode probe by which an increase in the outer diameter of a catheter can be reduced and which can be manufactured easily, and a method of manufacturing this probe.

To achieve the above object, the multielectrode probe of the present invention has the following arrangement.

That is, there is provided a multielectrode probe to be inserted into a patient, comprising a base on which a plurality of signal lines are tightly contacted, and an isolating coating and at least one electrode in each of the plurality of signal lines contacted on the base, wherein the electrodes are arranged on the base with predetermined spacings between them.

The multielectrode probe of the present invention has mechanical characteristics equivalent to those of a guide wire.

The multielectrode probe of the present invention transmits an intracardiac potential through the winding wires wound in a coil and each having the isolating coating with conductivity.

A practical method of manufacturing the multielectrode probe of the present invention is preferably a method by which a plurality of signal lines covered with isolating coatings are wound in a coil, and the isolating coating at a position at which an electrode is to be formed is stripped from each of the plurality of signal lines.

In addition, by winding a plurality of signal lines on a super elastic alloy wire, the multielectrode probe of the present invention can be given properties with which the probe gains a high torque transmissibility and hardly kinks (bends) even with a small diameter. In this case, since the wire itself is conductive, an isolating coating must be formed in advance on either the plurality of signal lines or the wire.

Furthermore, according to the multielectrode probe of the present invention, by winding a plurality of signal lines on a tube, such as a catheter tube, it is possible to measure an intracardiac blood pressure or to inject a liquid drug such as an antithrombotic drug simultaneously with the electrophysiology test.

Also, by winding a plurality of signal lines on a super elastic alloy tube, the multielectrode probe of the present invention can have the characteristics of both the super elastic alloy wire and a catheter.

A super elastic alloy herein mentioned is generally also called a shape-memory alloy and exhibits super elasticity at least at a patient temperature (around 37° C.). Preferable examples of the super elastic alloy are super elastic metal materials, particularly a Ti—Ni alloy containing 49 to 58 atm % of Ni, a Cu—Zn alloy containing 38.5 to 41.5 wt % of Zn, a Cu—Zn—X alloy (X=Be, Si, Sn, Al, or Ga) containing 1 to 10 wt % of X, and an Ni—Al alloy containing 36 to 38 atm % of Al. The super elastic alloy is most preferably the Ti—Ni alloy. The term "super elasticity" means a property with which a material restores its nearly original shape even when deformed (e.g., bent, stretched, or compressed) to such an extent that normal metals cause plastic deformations at application temperatures.

Another object of the present invention is to provide a method capable of readily manufacturing the multielectrode probe by reducing the number of manufacturing steps.

Still another object of the present invention is to provide a multielectrode probe which can be easily incorporated into a general catheter, and a method of manufacturing the same.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 5A and 5B are views for explaining how to use the multielectrode probe of the first embodiment, in which FIG. 5A is a sectional view showing a heart, and FIG. 5B is a sectional view showing the state in which the multielectrode probe of the first embodiment is used;

DESCRIPTION OF THE PREFERRED EMBODIMENTS

The preferred embodiments of the present invention will be described in detail below with reference to the accompanying drawings.

Before the explanation of the embodiments, the background of the use of the multielectrode probe of the present invention will be described. Tachycardiac arrhythmia, such as Wolff-Parkinson-White syndrome, often has an accessory pathway in addition to a normal conducting pathway in a heart. Therefore, it is necessary to locate the position of this accessory pathway. To find the accessory pathway present in the valve annulus of a heart, a probe is inserted into a right coronary artery running through the tricuspid annulus. At the same time, another probe is inserted from a coronary sinus into vena cordis magna. Consequently, the transmission of excitation from a pacing lead inserted into a left ventricle are measured simultaneously at a plurality of points. This makes it possible to find the accessory pathway within a short time period.

Figure 1:
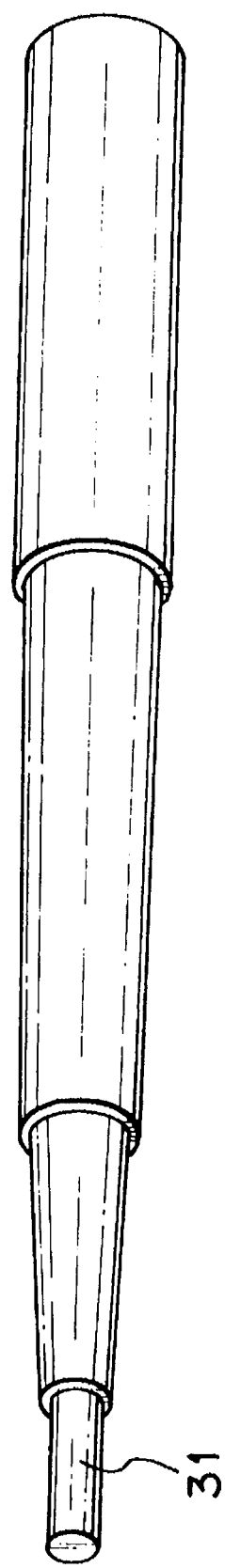
FIG. 1 is a perspective view showing the shape of a core wire of a multielectrode probe according to the first embodiment of the present invention.

FIG. 1 is a perspective view showing a super elastic alloy wire which is normally used as the core wire of a PTCA (Percutaneous Transluminal Coronary Angioplasty) guide wire and consists of an Ni—Ti alloy. Referring to FIG. 1, this core wire is tapered in accordance with characteristics such as a thrusting stiffness and a bending stiffness.

A cardiac probe with this shape can flexibly follow the complicated shape of vessel reaching a coronary artery or the like and can be readily inserted into the vessel system and intracardiac and removed therefrom.

Figure 2:
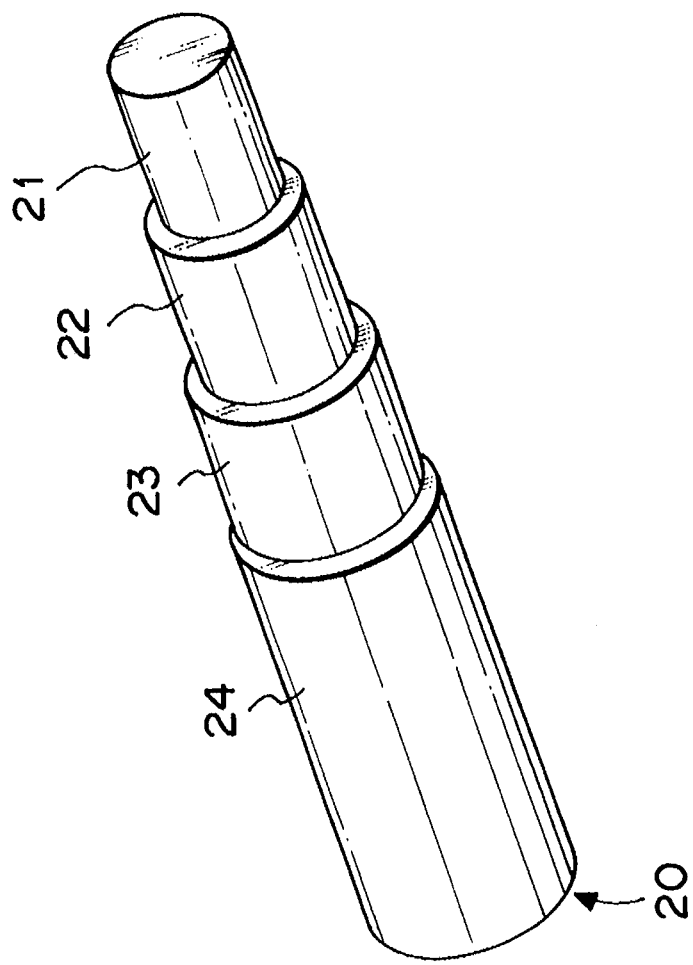
FIG. 2 is a perspective view for explaining the structure of a small-diameter wire (cladding wire) to be wound on the core wire.

FIG. 2 is a perspective view showing the structure of a small-diameter wire 20 to be wound in a multiple coil on the core wire of the guide wire illustrated in FIG. 1. This small-diameter wire 20 has a cladding structure and includes an isolating layer.

Referring numeral 21 denotes a carbon steel wire for keeping the strength of this small-diameter wire 20; 22, a copper foil layer for decreasing the impedance; 23, a gold-plating layer; and 24, an isolating layer consisting of a resin such as polyester. These parts may be made from some other materials, and it is not particularly necessary to use the cladding wire as the small-diameter wire.

This small-diameter wire (winding wire) 20 has almost no influence on the mechanical characteristics of the guide wire and does not degrade the characteristics that the core wire has as the guide wire. In addition, the use of the cladding material as the small-diameter wire 20 as the winding wire achieves effects of preventing breaking occurring in winding the winding wire on the core wire and decreasing the impedance of the winding wire to be as low as that of a normal copper wire.

To form a multielectrode probe having, e.g., twelve electrodes, twelve small-diameter wires (cladding wires) 20 are wound as a multiwire structure on the PTCA guide wire core wire 31. Since each of these small-diameter wires 20 is covered with the isolating coating 24 as shown in FIG. 2, they function as twelve independent intracardiac potential signal transmission lines.

Figure 6:
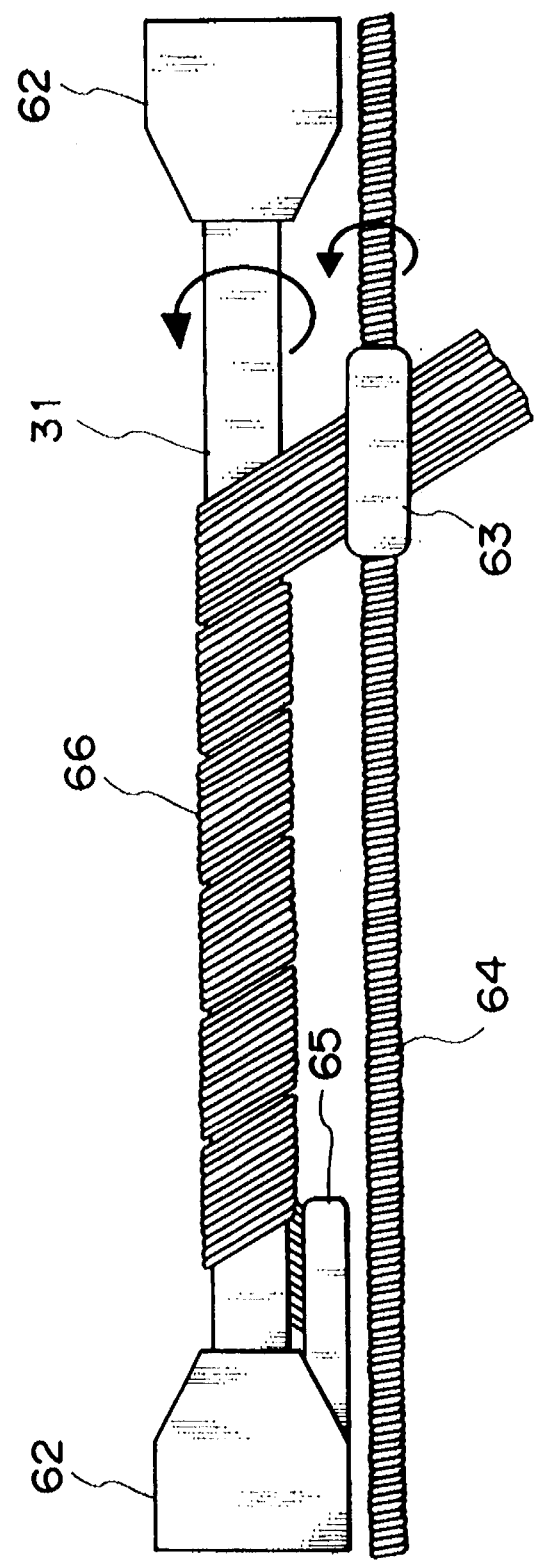
FIG. 6 is a view for explaining a method of manufacturing the multielectrode probe of the first embodiment.

FIG. 6 is a view for explaining a method of manufacturing the multielectrode probe of this embodiment.

Referring to FIG. 6, both the ends of the core wire 31 are fixed by a chuck 62 which is rotatable in the axial direction of the core wire 31. Subsequently, a winding wire 66 formed by binding twelve cladding wires 20 described above parallel to each other is fixed to a winding start chuck 65 through a winding wire guide 63. As shown in FIG. 6, this winding start chuck 65 is fixed to the chuck 62 for fixing the core wire 31 and rotated together with the core wire 31. The winding wire guide 63 is moved in the longitudinal direction of the core wire 31 by rotation of a guide feeder 64.

To wind the winding wire 66 including coil-like electrodes on the core wire 31 in this state, the core wire 31 is rotated, and the winding wire guide 63 is moved by rotating the guide feeder 64 in synchronism with the movement of the winding position of the winding wire 66 with respect to the core wire 31. The moving amount of the winding wire guide 63 is determined by the diameter of the core wire 31 and the width of the winding wire 66.

With the winding wire wound on the core wire 31 as described above, as shown in FIG. 3, the isolating coating 24 of a portion of these twelve cladding wires 20 is stripped by an amount of almost one circumference, exposing the gold-plating layer 23 inside the isolating coating 24 as indicated by reference numeral 33. Consequently, the conductive portion is exposed, and this exposed portion can be used as an intracardiac electrode. It is also possible to attach a ring-like electrode to this stripped portion 33 to widen the electrode area.

Figure 3:
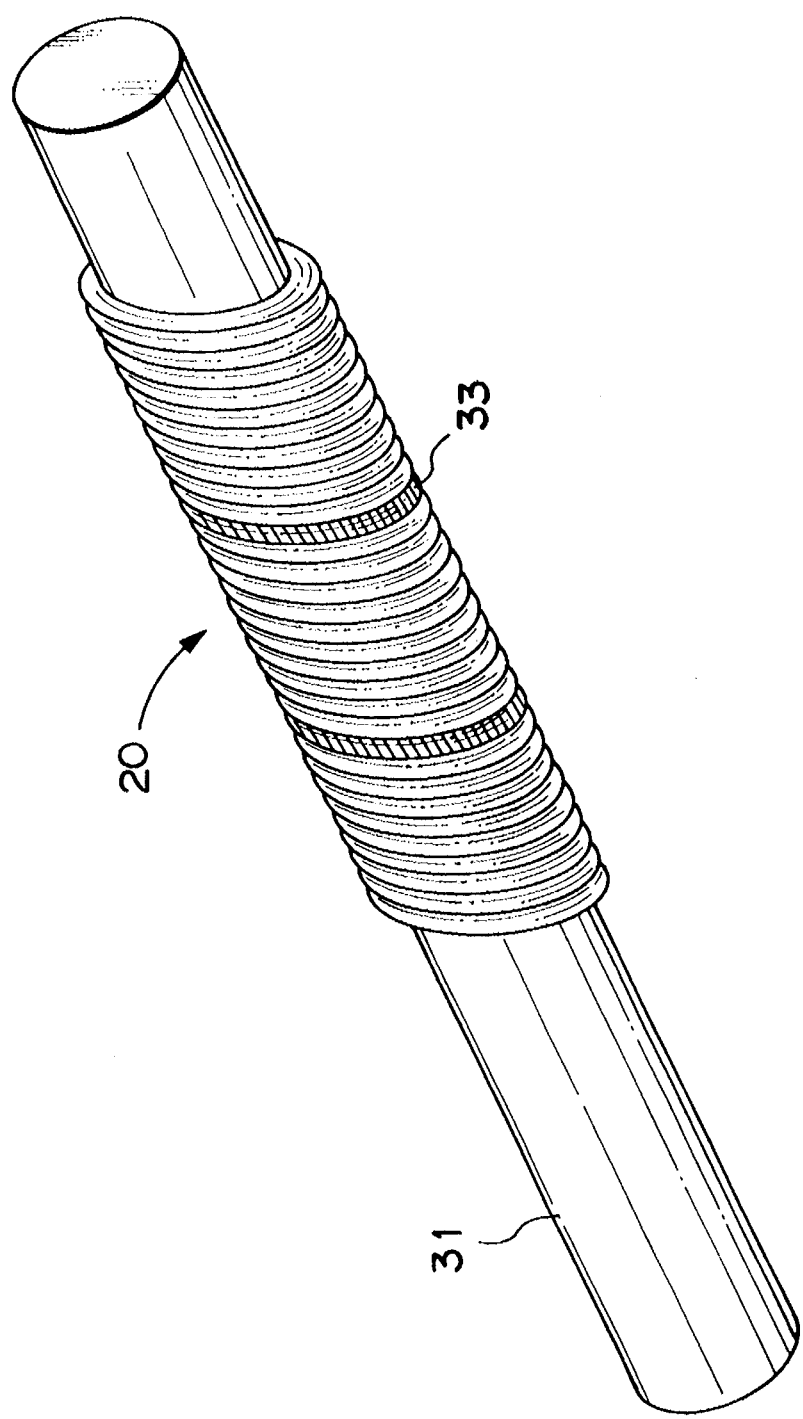
FIG. 3 is a perspective view for explaining the state in which the small-diameter wires (cladding wires) shown in FIG. 2 are wound in a multiple coil on the core wire and electrodes are formed.
Figure 4A:
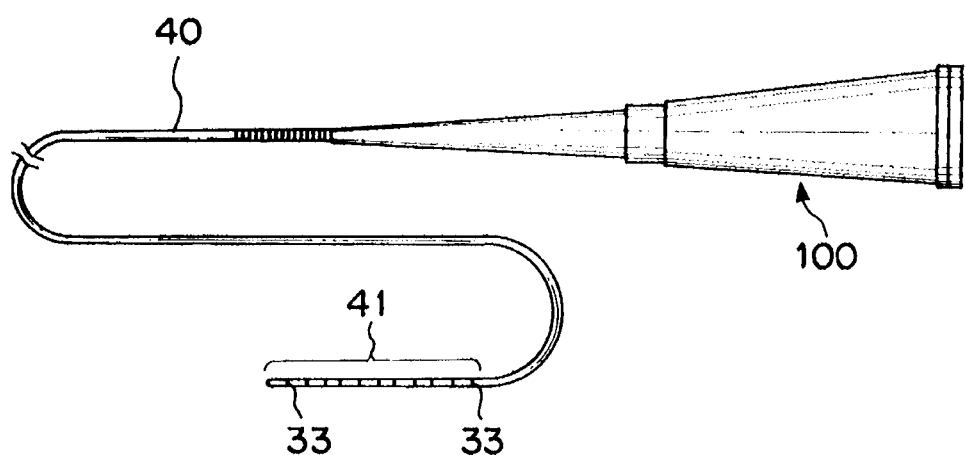
FIGS. 4A and 4B are views for explaining the outer appearance of the probe of the first embodiment and its equivalent circuit, respectively.

FIG. 4A is a view showing the outer appearance of a multielectrode probe 100 of this embodiment. In FIG. 4A, reference numeral 40 denotes a base of a portion of the probe to be inserted into a patient. The base 40 is constituted by winding the small-diameter wires (winding wires) 20 in a coil on the core wire 31. Reference numeral 41 denotes a portion in which the plurality of electrodes 33 are formed as shown in FIG. 3. In this embodiment, the electrodes 33 are formed with a spacing of about 2 mm. Assuming that the number of the winding wires 20 is 12, the length of this portion 41 is about 2.5 cm.

Figure 4B:
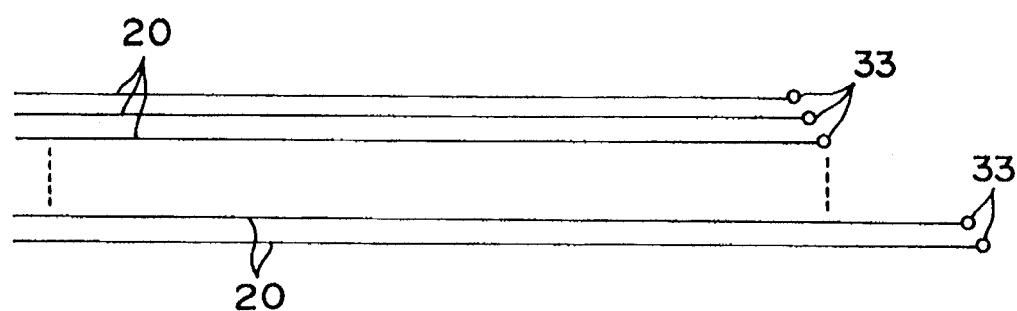

FIG. 4B is an equivalent circuit diagram of the signal lines and the electrodes of the multielectrode probe 100 of this embodiment. Referring to FIG. 4B, the electrodes 33 are formed in a one-to-one correspondence with the plurality of signal lines 20.

Figure 5A:
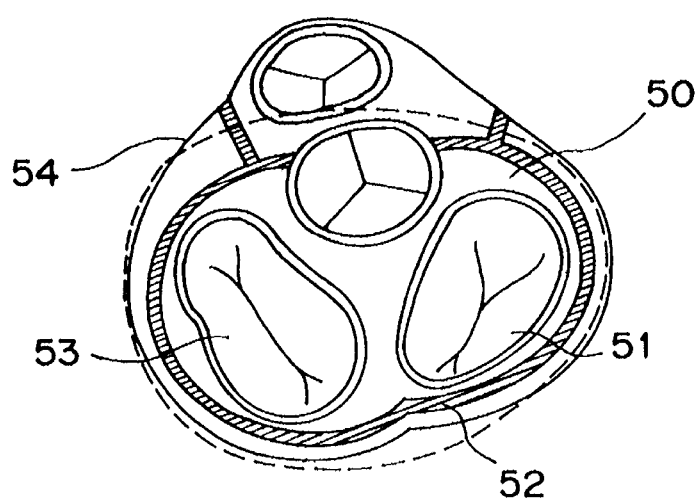
Figure 5B:
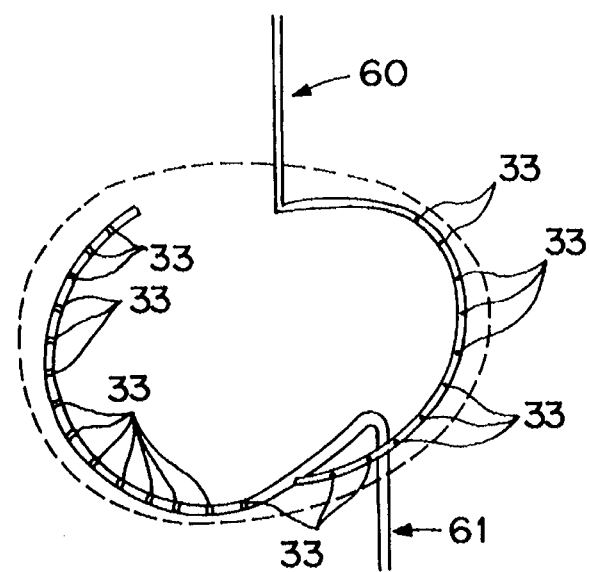

FIGS. 5A and 5B are views for explaining how to use the multielectrode cardiac probe of this embodiment.

FIG. 5A shows the sectional shape of a heart, in which reference numeral 50 denotes a right coronary artery into which one probe is inserted; 51, a tricuspid valve; 52, a coronary sinus into which another probe is inserted; 53, a mitral valve; and 54, an atrioventricular annulus.

FIG. 5B illustrates the state in which the probes of this embodiment are inserted into a cardiac artery and a cardiac vein.

Referring to FIG. 5B, reference numeral 60 denotes a probe for a right coronary artery; and 61, a probe for a left heart portion. Reference numerals 33 in FIG. 5B denote the electrode portions in each of which the isolating coating 24 mentioned earlier is stripped to expose the metal plating 23.

As described above, the number of electrodes can be increased without increasing the outer diameter of the cardiac probe for an electophysiology test. This makes it possible to shorten the examination time and to decrease the number of probes to be used. In addition, the use of the small-diameter probe facilitates inserting the probe into a right coronary artery.

Also, in the multielectrode probe of this embodiment, the distance between the electrodes can be decreased. Consequently, the detection accuracy for an accessory pathway can be increased.

Furthermore, in the probe of this embodiment, the signal lines and the electrodes need not be connected since they are formed integrally with each other. This simplifies the manufacturing process.

Note that the portion other than the electrodes may be covered with a certain another material in order to allow smooth motion in vessels. Note also that the core wire 31 is not limited to the PTCA guide wire, but the thickness, the material, and the like of the core wire can naturally be altered.

In addition, the number of small-diameter wires to be wound is not limited to that used in this embodiment but can be properly selected. Furthermore, if a sufficient strength can be obtained by the small-diameter wires wound in a coil, the core wire can be omitted.

There is another possible method by which after a plurality of signal lines each covered with an isolating coating are wound in a coil, a conductive metal foil, such as a gold foil, is wound on the signal lines and welded to positions at which electrodes are to be formed by using a laser or the like. In this method, however, it is difficult to locate these prospective electrode formation positions through the metal foil.

As an alternative, therefore, a plurality of signal lines not covered with an isolating coating are wound in a coil with given spacings between them so as not to contact each other, and then an isolating coating is formed on a portion other than positions at which electrodes are to be formed.

Figure 7:
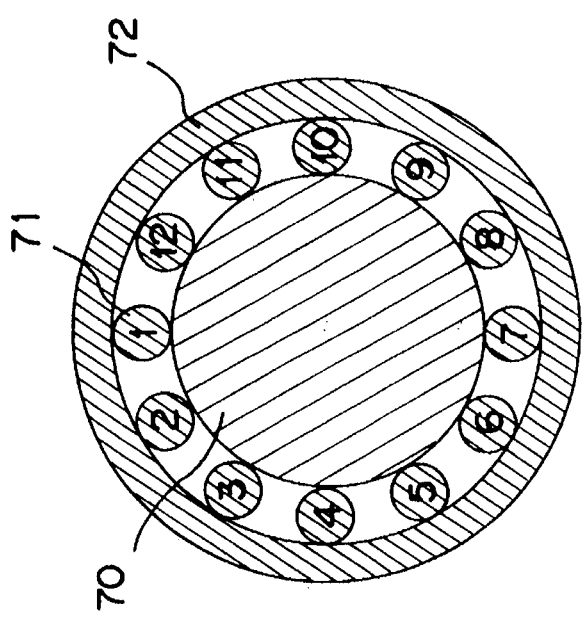
FIG. 7 is a sectional view showing a multielectrode probe according to the second embodiment of the present invention.
Figure 8:
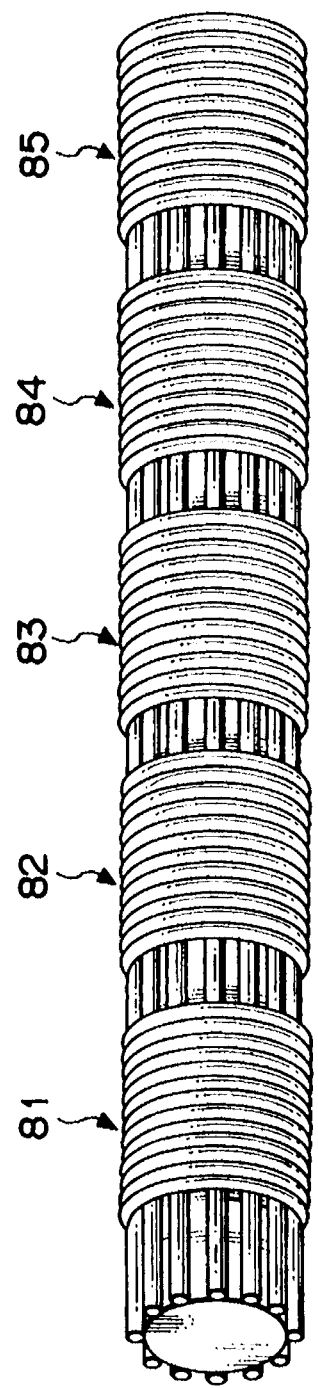
FIG. 8 is a perspective view showing the outer appearance of the multielectrode probe of the second embodiment.

FIGS. 7 and 8 are views showing the arrangement of a multielectrode probe according to the second embodiment of the present invention.

Figure 9:
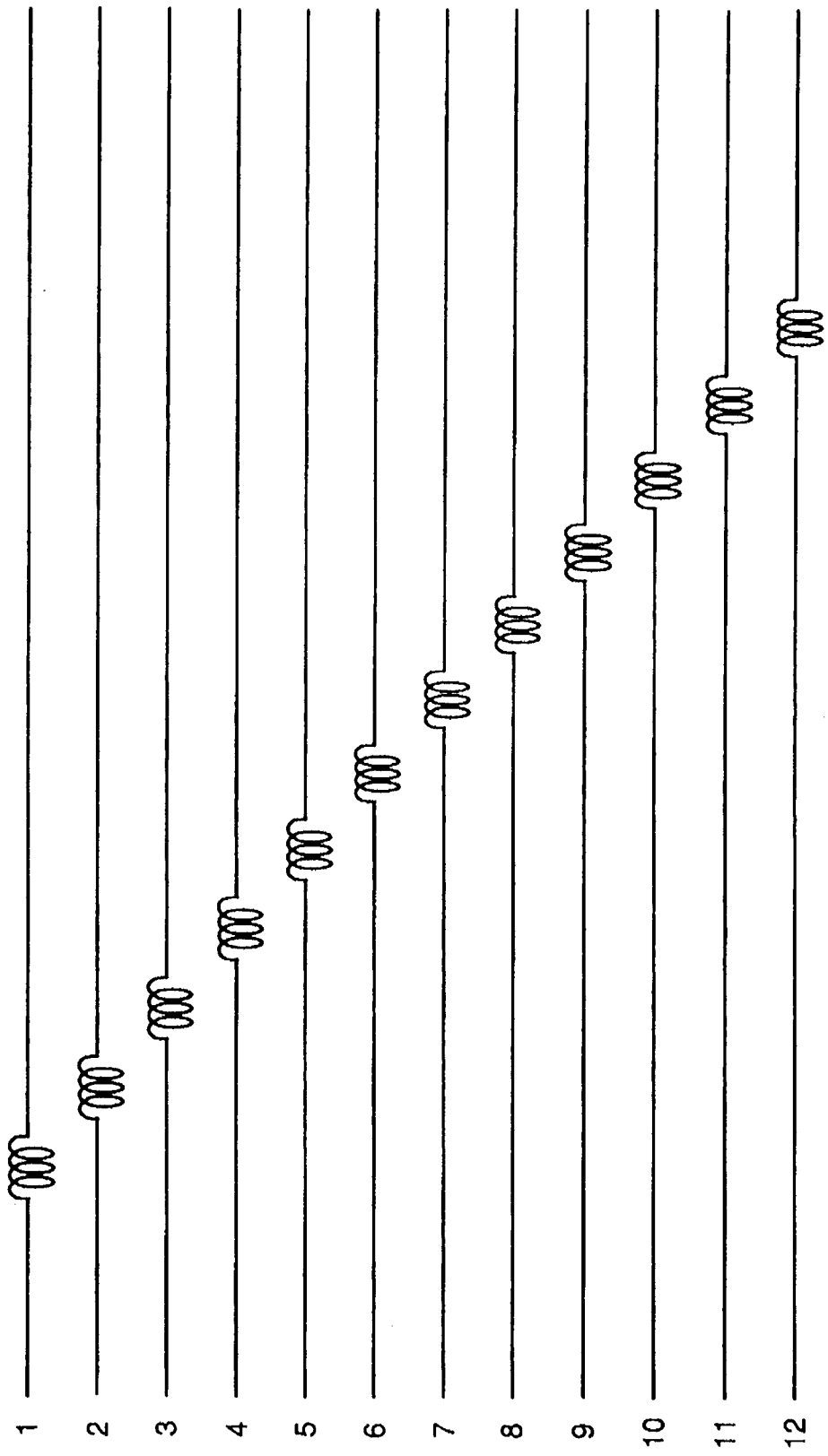
FIG. 9 is a typical diagram of each lead wires of the multielectrode probe of the second embodiment.

As illustrated in the sectional view of FIG. 7, twelve lead wires 71 are extended along a base 70, and isolated portions of these lead wires 70 are stripped at positions at which electrodes are to be formed. The portions 72 from which the isolated portions are stripped are wound in a single coil as shown in FIG. 8, and then the lead wires 71 are again extended linearly. Consequently, a multielectrode probe having electrodes each with a certain width is formed. By repeatedly executing this manipulation by the number of lead wires, a multielectrode probe with a desired electrode width can be formed. In FIG. 8, reference numeral 81 denotes an electrode formed by stripping the isolated portion of the first lead wire 71; 82, an electrode formed by stripping the isolated portion of the second lead wire; 83, an electrode formed by stripping the isolated portion of the third lead wire, and the like. FIG. 9 is a typical diagram of each lead wires of this multielectrode probe. Note that the lead wires are extended linearly in FIG. 8, but the present invention is not limited to this arrangement. That is, as in the above embodiment, these lead wires can also be wound in a multiple coil on the base.

Figure 10:
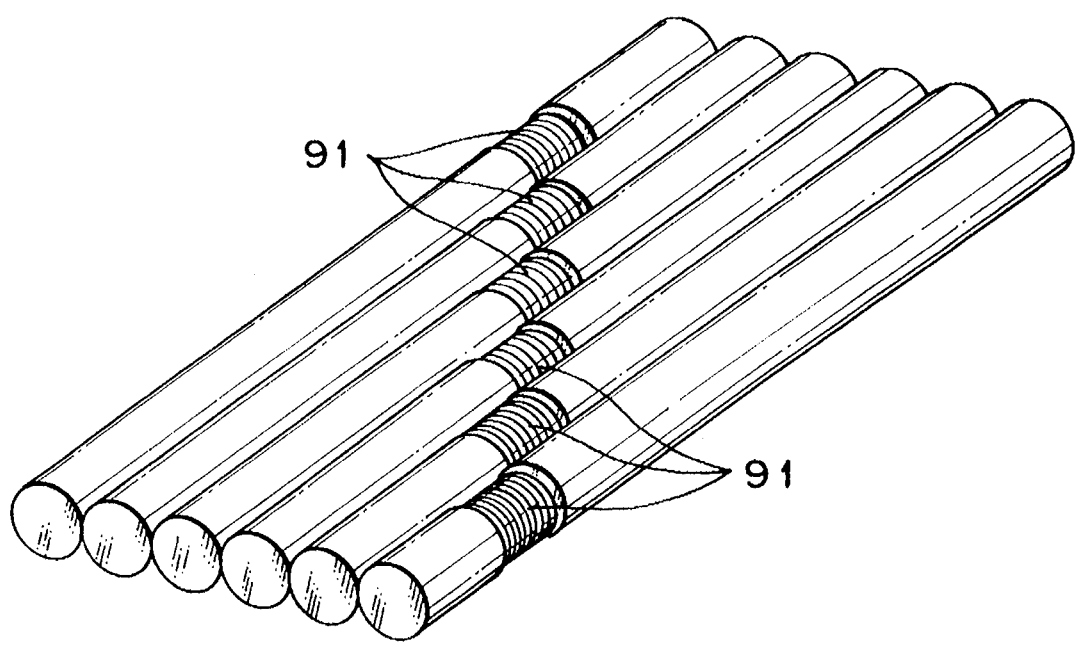
FIG. 10 is a perspective view showing the shape of a signal line of a multielectrode probe according to the third embodiment of the present invention.

FIG. 10 is a view showing the arrangement of a signal line of a multielectrode probe according to the third embodiment of the present invention.

In this embodiment, a necessary number of conductor wires (lead wires) are arranged parallel to each other as shown in FIG. 10, thereby forming a generally known flat cable. An isolating layer of the cable is stripped by performing laser processing or the like for portions requiring electrodes. In FIG. 10, reference numerals 91 denote electrodes thus formed. Electrode contacts and conductor wire portions can be formed by winding the resulting flat cable on a base at a certain predetermined angle with respect to the base as shown in FIG. 6. It is also possible, if necessary, to form an electrode with a certain width by electrically adhering a ring-like electrode to the portion from which the isolating layer is stripped by performing, e.g., welding.

The cable shown in FIG. 10 can also be extended along the longitudinal direction of the base, e.g., extended along the surface shape of the base as shown in FIG. 8. In this arrangement, as in the above arrangement, an electrode having a certain width can be formed by electrically adhering a ring-like electrode to a portion from which the isolating layer is stripped by performing welding or the like.

Alternatively, with an adhesive layer coated on the surface of the base, conductor wires whose isolating layer is stripped from portions requiring electrodes are adhered parallel to the base. In addition, ring-like electrodes are electrically adhered to the portions from which the isolating layer is stripped by performing, e.g., welding as needed. As a result, an electrode having a certain width can be formed. It is also possible to adhere the conductor wires to the base by coating an adhesive on the conductor wires.

Figure 11:
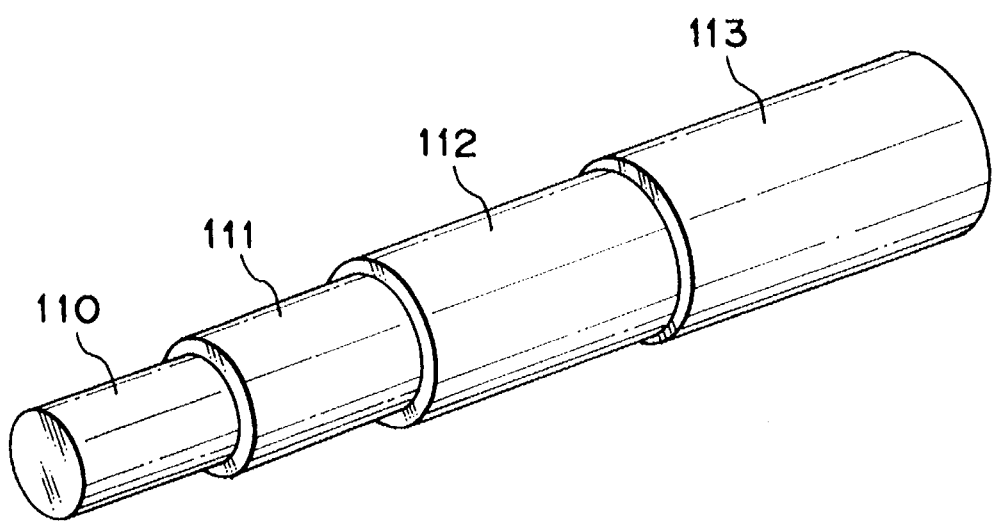
FIG. 11 is a perspective view for explaining the arrangement of a multielectrode probe according to the fourth embodiment of the present invention.

FIG. 11 is a view showing the arrangement of a multielectrode probe according to the fourth embodiment of the present invention. Referring to FIG. 11, an isolating layer 111 and a conductor layer 112 are vapor-deposited on a base 110. The conductor layer 112 is then spirally divided by performing etching or laser processing. Subsequently, an isolating layer is formed on the conductor layer 112 except for portions to be formed into electrodes. If necessary, ring-like electrodes are electrically adhered to the portions on which no isolating layer is formed by performing welding or the like. Consequently, an electrode with a certain width can be formed.

Alternatively, the same number of conductor wires as the number of electrodes to be formed are extended linearly on a printed wiring sheet which is generally called a flexible print circuit (FPC) formed by using polyimide as a base. In addition, if necessary, ring-like electrodes are electrically adhered to portions from which an isolating layer is stripped by performing welding or the like. This makes it possible to form an electrode having a certain width. It is also possible to form a larger number of electrodes by winding the plurality of flexible substrates.

According to the embodiments of the present invention, as has been described above, a multielectrode cardiac probe for use in an electrophysiology test of a heart can be realized with mechanical characteristics and a thickness analogous to those of a PTCA guide wire. In addition, a number of electrodes can be formed easily.

Furthermore, the probe of the present invention can be inserted into a right coronary artery, which is difficult to realize by conventional probes. Consequently, an intracardiac potential can be measured simultaneously at a plurality of points. This shortens the examination time and improves the accuracy at which the position of an accessory pathway is located.

Other many widely different embodiments of the present invention can be made without departing from the spirit and scope thereof, it is to be understood that the invention is not limited to the specific embodiments thereof except as defined in the appended claims.

What is claimed is:

1. A multielectrode probe to be inserted into a living body, comprising:

a plurality of signal lines in tight contact with a surface of a base that is made of a super elastic alloy, wherein each of said plurality of signal lines in tight contact with the surface of said base has an isolating coating and at least one electrode, and said electrodes are arranged on said base with predetermined spacings therebetween.

2. The probe according to claim 1, wherein said electrodes are formed by stripping said isolating coatings of said plurality of signal lines.

3. The probe according to claim 1, wherein said electrodes are ring-like electrodes connected to said plurality of signal lines.

4. The probe according to claim 1, wherein each of said plurality of signal lines has a cladding structure.

5. The probe according to claim 1, wherein said base is a catheter tube.

6. The probe according to claim 1, wherein said super elastic alloy is a Ti—Ni alloy containing 49 to 58 atm % of Ni.

7. The probe according to claim 1, wherein said super elastic alloy is a Ti—Ni alloy containing 49 to 58 atm % of Ni.

8. The probe according to claim 1, wherein said plurality of signal lines are wound in a coil on said base.

9. The probe according to claim 1, wherein said plurality of signal lines are adhered on said base along a longitudinal direction thereof.

10. The probe according to claim 1, wherein said super elastic alloy is a Cu—Zn alloy containing 38.5 to 41.5 wt % of Zn.

11. The probe according to claim 1, wherein said super elastic alloy is a Cu—Zn—Be alloy containing 1 to 10 wt % of Be.

12. The probe according to claim 1, wherein said super elastic alloy is a Cu—Zn—Si alloy containing 1 to 10 wt % of Si.

13. The probe according to claim 1, wherein said super elastic alloy is a Cu—Zn—Sn alloy containing 1 to 10 wt % of Sn.

14. The probe according to claim 1, wherein said super elastic alloy is a Cu—Zn—Al alloy containing 1 to 10 wt % of Al.

15. The probe according to claim 1, wherein said super elastic alloy is Cu—Zn—Ga alloy containing 1 to 10 wt % of Ga.

16. The probe according to claim 1, wherein said super elastic alloy is a Ni—Al alloy containing 36 to 38 atm % of Al.

17. A multielectrode probe to be inserted into a living body, comprising:

a plurality of signal lines in tight contact with a surface of a base which is made of a super elastic alloy, wherein each of said plurality of signal lines in tight contact with the surface of said base has an isolating coating and at least one non-coated portion as an electrode, and said non-coated portions of said plurality of signal lines are arranged on said base with predetermined spacings therebetween.

* * * * *